US008373855B2

(12) United States Patent
Fink et al.

(10) Patent No.: US 8,373,855 B2
(45) Date of Patent: Feb. 12, 2013

(54) COMPACT RAMAN ANALYZER FOR RECORDING DISSOLVED GASES IN LIQUIDS WITH HIGH SENSITIVITY AND SPECTRAL RESOLUTION

(75) Inventors: Manfred Fink, Austin, TX (US); Philip Varghese, Austin, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/016,966

(22) Filed: Jan. 29, 2011

(65) Prior Publication Data
US 2012/0026494 A1 Feb. 2, 2012

Related U.S. Application Data

(60) Provisional application No. 61/299,519, filed on Jan. 29, 2010.

(51) Int. Cl.
G01N 3/44 (2006.01)
(52) U.S. Cl. ........................................ 356/301; 356/246
(58) Field of Classification Search .................. 356/301, 356/246
See application file for complete search history.

(56) References Cited

U.S. PATENT DOCUMENTS

| 4,633,103 | A | | 12/1986 | Hyman |
| 4,953,976 | A | * | 9/1990 | Adler-Golden et al. ....... 356/301 |
| 5,754,288 | A | | 5/1998 | Yamamoto |
| 5,786,893 | A | * | 7/1998 | Fink et al. ..................... 356/301 |
| 5,929,453 | A | | 7/1999 | Andrews et al. |
| 6,307,626 | B1 | | 10/2001 | Miles |
| 6,778,269 | B2 | | 8/2004 | Fink |
| 6,795,177 | B2 | * | 9/2004 | Doyle ............................ 356/301 |
| 7,800,751 | B1 | * | 9/2010 | Silver et al. ................... 356/246 |
| 2009/0306527 | A1 | | 12/2009 | Kubo |
| 2011/0218431 | A1 | | 9/2011 | Fink |

FOREIGN PATENT DOCUMENTS

| BR | 11 2012 018936 0 | 7/2012 |
| EP | 11737711.9 | 8/2012 |
| EP | 11737800.0 | 8/2012 |
| IN | 7410/DELNP/2010 | 8/2012 |
| JP | 2001-215194 A | 8/2001 |
| RU | 2012136878 | 8/2012 |
| WO | WO/2011/094513 | 8/2011 |
| WO | WO/2011/094651 | 8/2011 |

OTHER PUBLICATIONS

International Search Report for International Application No. PCT/US2011/023074 (mailed Sep. 22, 2011).
U.S. Appl. No. 61/299,519, filed Jan. 29, 2010, Manfred Fink.
U.S. Appl. No. 61/299,555, filed Jan. 29, 2010, Manfred Fink.
International Preliminary Report on Patentability and Written Opinion issued Jul. 31, 2012 for WO/2011/094651 (PCT/US2011/023074) (4 pages).
Non-Final Office Action mailed May 30, 2012 for U.S. Patent Publication No. 2011/0218431 (U.S. Appl. No. 13/015,878) (6 pages).

* cited by examiner

Primary Examiner — Layla Lauchman
(74) Attorney, Agent, or Firm — Ballard Spahr LLP

(57) ABSTRACT

A Raman head is provided capable of operating at high surrounding pressures. The Raman head has housing having a first, sealed chamber filled with an incompressible liquid and a second chamber that is open to the surrounding environment. At least one bellows can be used to equalize pressure between the first sealed chamber and the surrounding environment. A planar side of a pair of plano-concave lens is positioned within the first chamber and the concave side of each plano-concave lens is positioned within the second chamber of the Raman head. Light emitted as a result of a laser beam in communication with the pair of plano-concave lens can be analyzed by a Raman analyzer.

7 Claims, 3 Drawing Sheets

COMPACT RAMAN ANALYZER FOR RECORDING DISSOLVED GASES IN LIQUIDS WITH HIGH SENSITIVITY AND SPECTRAL RESOLUTION

CROSS-REFERENCE TO RELATED APPLICATIONS

This application claims priority to U.S. Provisional Patent Application Ser. No. 61/299,519, filed Jan. 29, 2010, which is hereby incorporated by reference in its entirety for all purposes.

FIELD

Provided is a Raman head for a Raman spectrometer for recording dissolved gases in liquids. More specifically, a Raman head is provided for positioning and protecting a Raman cell capable of operating under high ambient pressures in a liquid medium such as water.

BACKGROUND

Raman scattering is a type of inelastic scattering of electromagnetic radiation, such as visible light, discovered in 1928 by Chandrasekara Raman. When a beam of monochromatic light is passed through a substance some of the radiation will be scattered. Although most of the scattered radiation will be the same as the incident frequency ("Rayleigh" scattering), some will have frequencies above ("anti-Stokes" radiation) and below ("Stokes" radiation) that of the incident beam. This effect is known as Raman scattering and is due to inelastic collisions between photons and molecules that lead to changes in the vibrational and rotational energy levels of the molecules. This effect is used in Raman spectroscopy for investigating the vibrational and rotational energy levels of molecules. Raman spectroscopy is the spectrophotometric detection of the inelastically scattered light.

"Stokes" emissions have lower energies (lower frequencies or a decrease in wave number ($cm^{-1}$)) than the incident laser photons and occur when a molecule absorbs incident laser energy and relaxes into an excited rotational and/or vibrational state. Each molecular species will generate a set of characteristic Stokes lines that are displaced from the excitation frequency (Raman shifted) and whose intensities are linearly proportional to the density of the species in the sample.

"Anti-Stokes" emissions have higher frequencies than the incident laser photons and occur only when the photon encounters a molecule that, for instance, is initially in a vibrationally excited state due to elevated sample temperature. When the final molecular state has lower energy than the initial state, the scattered photon has the energy of the incident photon plus the difference in energy between the molecule's original and final states. Like Stokes emissions, anti-Stokes emissions provide a quantitative fingerprint for the molecule involved in the scattering process. This part of the spectrum is seldom used for analytical purposes since the spectral features are weaker. However, the ratio of the Stokes to the anti-Stokes scattering can be used to determine the sample temperature if it is in thermal equilibrium.

The Stokes and anti-Stokes emissions are collectively referred to as spontaneous "Raman" emissions. Since the excitation frequency (near infrared) and the frequency of the Stokes (and anti-Stokes) scattered light are typically far off the resonance of any component in the sample, fluorescence at frequencies of interest is minimal. The sample is optically thin and will not alter the intensities of the Stokes emissions (no primary or secondary extinctions), in stark contrast to infrared absorption spectroscopy.

Raman spectroscopy is a well-established technology to determine the presence of trace compounds and their isotopomers down to one part per million levels within a host of mixtures. With Raman analysis, absolute concentrations can be determined, the sparse spectra minimize interferences of overtones and combination lines since they are strongly suppressed.

However, conventional Raman spectrometers can require tuning of the incident laser frequency. Additionally, conventional Raman analyzers can lack the desired sensitivity, require an extensive integration time, be too large and/or be too costly for widespread use. Thus, there is a need in the art for a relatively inexpensive, compact Raman spectrometer capable of improved sensitivity and integration times, and capable of operating at high surrounding pressures (up to 800 bars).

SUMMARY

In accordance with the purpose(s) of this disclosure, as embodied and broadly described herein, in one aspect, a Raman head is provided capable of operating at high surrounding pressures which might occur, for example, at depths in the ocean. In another aspect, the Raman head comprises a Raman housing comprising a first, sealed chamber filled with a liquid medium, such as, for example and without limitation, distilled water, and a second chamber open to the surrounding environment. In another aspect, the first chamber and the second chamber can be separated by a window that is transmissive for laser light.

In one aspect, the Raman head can further comprise a multi-pass Raman cell comprising a pair of opposed plano-concave lenses. In another aspect, a planar side of each lens of the pair of plano-concave lenses can be positioned substantially parallel and adjacent to the planar side of the opposed lens. In another aspect, the planar side of each plano-concave lens can be positioned within the first chamber of the Raman head, and the concave side of each plano-concave lens can be positioned within the second chamber of the Raman head. In still another aspect, the concave side of each plano-concave lens can be coated such that the plano-concave lenses act as mirrors.

In one aspect, the Raman head further comprises at least one bellows configured to equalize the pressure between the first sealed chamber and the surrounding environment. Because the liquid medium of the first sealed chamber can be nearly incompressible, the required adjustments by the at least one bellows can be de minimis.

Additional advantages will be set forth in part in the description which follows, and in part will be obvious from the description, or may be learned by practice of the aspects of the disclosure as described herein. The advantages can be realized and attained by means of the elements and combinations particularly pointed out in the appended claims. It is to be understood that both the foregoing general description and the following detailed description are exemplary and explanatory only and are not restrictive of the aspects of the disclosure, as claimed.

BRIEF DESCRIPTION OF THE DRAWINGS

The accompanying drawings, which are incorporated in and constitute a part of this specification, illustrate aspects of the disclosure and, together with the description, serve to explain the principles of the disclosure.

DETAILED DESCRIPTION

The present disclosure may be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to an "analyzer" can include two or more such analyzers unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to certain embodiments of the disclosure, examples of which are illustrated in the accompanying drawings. Wherever possible, the same reference numbers are used throughout the drawings to refer to the same or like parts.

In one aspect, a Raman head 10 is provided for use in a Raman spectrometer, such as that described in U.S. Pat. No. 6,778,269, which is incorporated by reference herein in its entirety.

Figure 1:
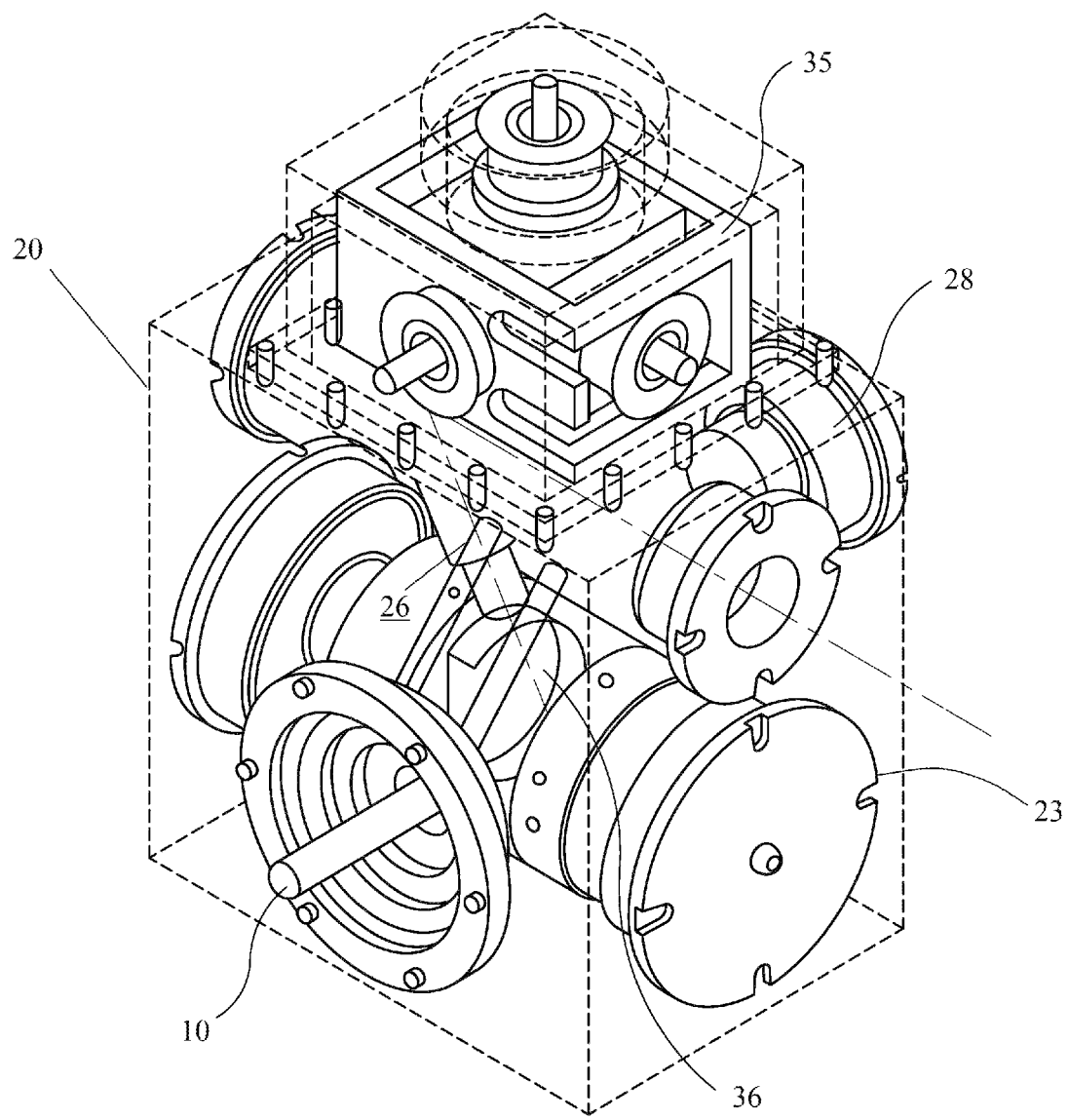
FIG. 1 is a perspective view of an assembled Raman head, according to one aspect.
Figure 2:
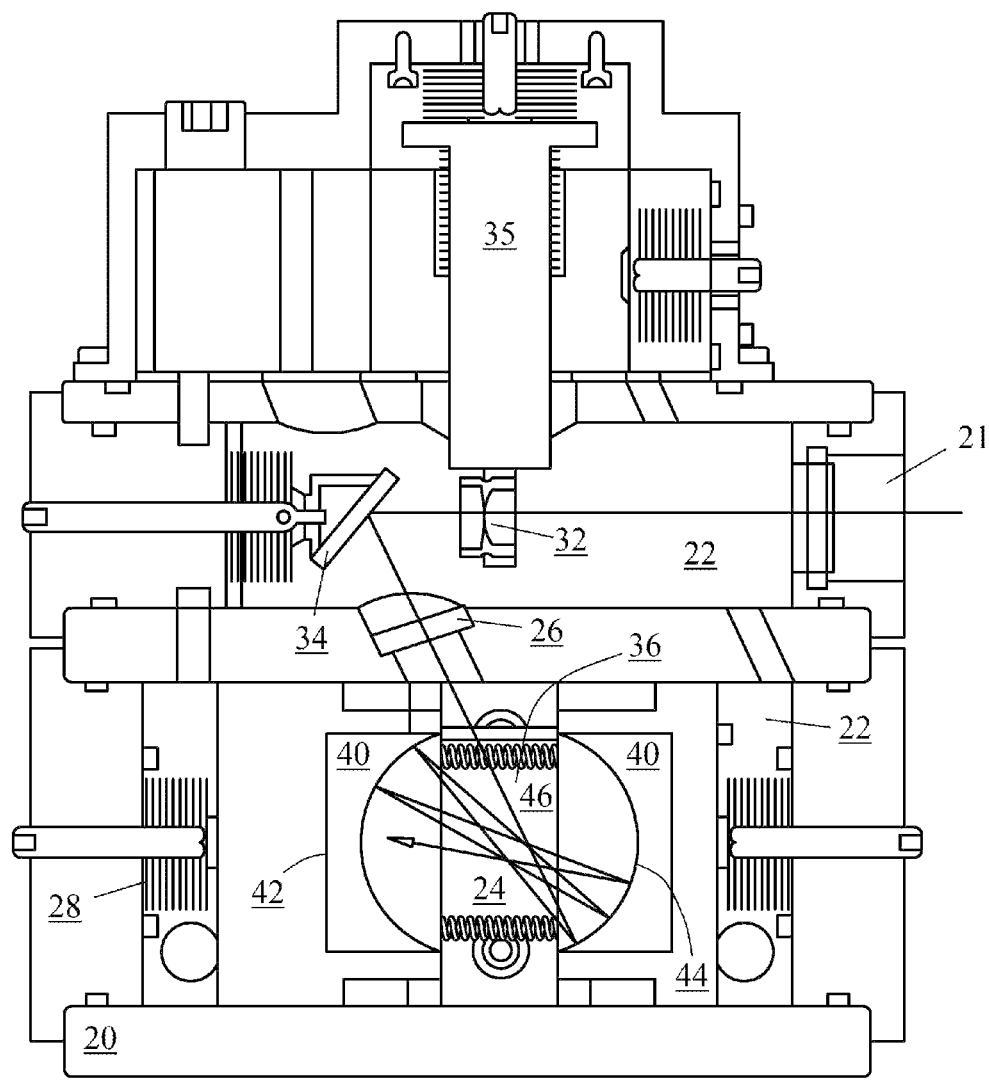
FIG. 2. is a side cross-sectional view of the Raman head of FIG. 1.

As illustrated in FIGS. 1-2, the Raman head 10 can comprise a Raman housing 20. According to one aspect, the Raman housing 20 can be formed from an inert metal such as 316 stainless steel, titanium, and the like. In one aspect, the Raman housing can define a first, sealed chamber 22 and a second chamber 24 that is configured to be open to or otherwise in communication with the surrounding medium. In another aspect, the second chamber can be positioned in a central portion of the housing and can be sized to hold a Raman cell 36. The first chamber 22 can, in one aspect, have a proximal end defining an aperture 21, a central portion, and a distal end. The aperture can have an entry window therein configured for receiving a laser beam originating outside the Raman housing 20 therethrough. In another aspect, a first port 23 can be defined in the housing to provide an inlet to the first chamber for a predetermined fluid, and a second port 25 can be defined in the housing to provide an inlet to the second chamber for a sample medium. In another aspect, a window 26 can separate the first chamber from the second chamber 24.

As will be described more fully below, in use, the second chamber can be open to the environment surrounding the Raman head and can fill with the surrounding medium for analysis. Because the second chamber is open to the medium of the environment, pressure in the second chamber 24 is in substantial equilibrium with the surrounding medium. In another aspect, the first chamber of the housing can be filled with a predetermined fluid, such as for example and without limitation, distilled water. In this aspect, it is contemplated that the predetermined fluid can be a substantially incompressible fluid.

In one aspect, the Raman head 10 can further comprise at least one bellows 28 configured for passively adjusting the pressure in the first sealed chamber 22. In another aspect, the at least one bellows can be formed from an inert metal, such as, for example and without limitation, 316 stainless steel, titanium, and the like. In another aspect, the at least one bellows 28 can be configured to transfer pressure from outside the Raman head 10 to the predetermined fluid inside the first chamber. Thus, in one aspect, the pressure inside the first chamber 22 can be passively balanced by the at least one bellows. As one skilled in the art will appreciate, the required adjustments by the at least one bellows can be de minimis when the predetermined fluid is substantially incompressible.

In one aspect, the window 26 is formed of a material which is transmissive for laser light such as, for example and without limitation, sapphire. It is contemplated that the window can be formed of a material and have a thickness that is sufficient to withstand the pressure differences applied by the medium.

Figure 3:
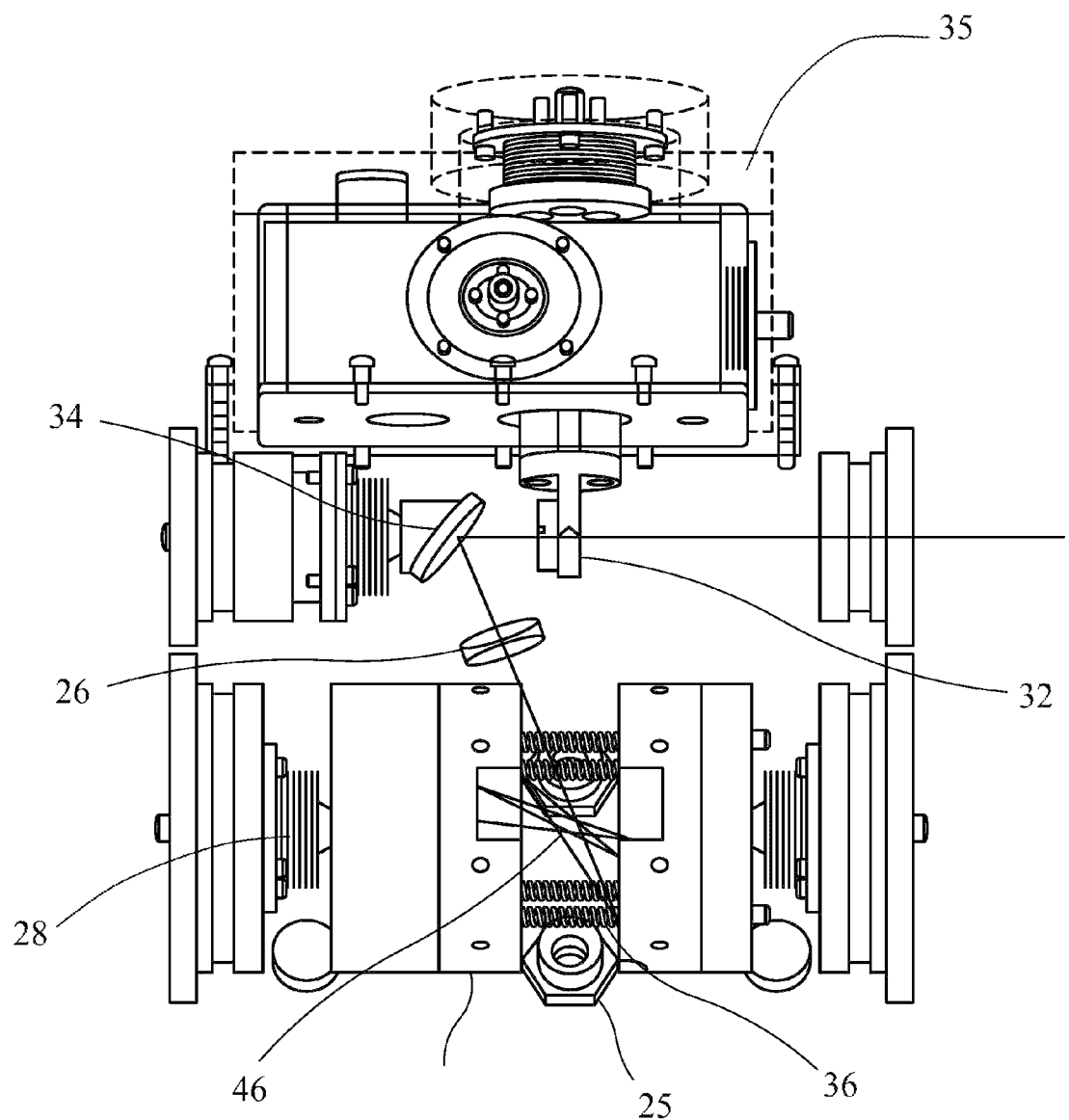
FIG. 3 is an exploded perspective view of the Raman head of FIG. 1 without a Raman housing, according to one aspect.

According to one aspect, the Raman head 10 can further comprise an achromatic lens 32 that is positioned in the center portion of the first chamber 22 of the Raman housing 20 and a mirror 34 that is positioned on the distal end of the first chamber. In another aspect, the achromatic lens can be adjusted by an adjusting assembly 35, as illustrated in FIG. 3. In this aspect, the adjusting assembly can be configured to selectively adjust the position of the achromatic lens in one, two, and/or three dimensions in order to optimize the focusing condition of the achromatic lens 32. In use, the achromatic lens 32 can guide a focused NIR laser beam via the mirror through the window 26 into the second chamber 24.

In one aspect, the Raman head 10 further comprises a multi-pass Raman cell 36 comprising two plano-concave lenses 40 positioned in opposition to each other. In another aspect, each plano-concave lens can have a planar side 42 and a concave side 44. In another aspect, each lens of the two plano-concave lenses can be formed from glass, such as for example and without limitation, BK-7 glass. In another aspect, the planar side 42 of each lens 40 can be positioned substantially parallel to each other in the first chamber 22. The concave side of the lenses may be gold coated to form mirrors with a reflectivity of approximately 98.5% for NIR wavelengths. As can be appreciated by one of skill in the art, the radius of curvature of the respective plano-concave lenses can dictate the relative spacing between the lenses. In this aspect, the spaced plano-concave lenses define an interior cavity 46.

In one aspect, because the planar side 42 of each plano-concave lens is positioned in the first chamber, the planar sides of the opposed plano-concave lenses 40 are in contact only with the predetermined liquid medium. Thus, in another aspect, the planar sides of the concave lenses can be uncoated. In another aspect, the concave sides of the lenses are positioned in the second chamber 24 of the housing and are in contact only with the surrounding fluid that fills the second chamber. In this aspect, then, the concave sides of the lenses can therefore be coated with at least one protective layer. In another aspect, at least a portion of the concave side of each lens 40 can be coated with at least one gold protective layer to form a mirrored surface. In another aspect, the at least one protective gold layer of the concave side 44 of the lenses 40 can be about 200 nm thick, though it is of course contemplated that the thickness of the at least one gold layer can be greater than or less than 200 nm thick.

In one aspect, the concave lenses 40 can act as spherical mirrors in a multi-pass arrangement. The propagation of a laser beam between the concave surfaces 44 generates many passes with two common focal points at or near the center of the Raman cell 36.

In operation, because the second chamber 24 of the Raman housing 20 is open to the environment surrounding the housing, fluid from outside the Raman housing 20 can enter the interior lens cavity 46 through the second port 25 of the housing. In one aspect, a focused laser beam entering the second chamber 24 through the window 26 can reflect off the first plano-concave lens 40 to the second plano-concave lens. Up to 50 passes of the laser beam through the fluid in the Raman cell 36 can be achieved, when the laser beam foci are located near a center of the lens cavity. In one aspect, two crossing points can be formed (one crossing point from all beams coming from the concave side 44 of the first lens; and the other crossing point from the beams coming from the convex side of the second lens) inside a volume of about $1 \times 1 \times 0.2$ mm$^3$ each. The crossing points are the scattering centers for the Raman light.

In one aspect, the light scattered from the focal areas and the surroundings can be collected with a collecting lens with relatively large numerical apertures, such as, for example and without limitation, f/0.9. In this aspect, the collected light can form images of the two focal points outside the Raman cell 36. In another aspect, a double aperture can allow the Raman light to pass and reject all stray light which originates from the cell at large. An imaging lens can image the two apertures to infinity and the two highly overlapping beams of scattered light can enter a compartment to be analyzed by a Raman analyzer, as described in U.S. Pat. No. 6,778,269 and/or U.S. Provisional Patent Application 61/299,555, which is hereby incorporated by reference for all purposes.

The arrangement of the Raman head 10 as described herein can be easy to set up and to keep clean, preventing bio-sludge from coating the optics and diminishing the performance of the Raman cell 36.

In certain aspects, the Raman head 10 can be used to non-invasively test for the conversion of an isotopically labeled substrate, such as, for example and without limitation, $^{12}CO_2$, $^{13}CO_2$, $NH_4^{14}NO_3$, $NH_4^{13}NO_3$, $H_2$, HD, $D_2$, and the like. In one aspect, optical spectroscopy provides a diagnostic tool to evaluate the level of $CO_2$ dissolved in water at large depth.

For the determination of $CO_2$ dissolved in water at large depth, the Raman lines of $CO_2$ are broadened, but the widths of the spectral lines are independent of the submersion depths. Similar results have been reported for $O_2$, $N_2$, $N_2O$ and $NH_3$. It is contemplated that a plurality of Raman heads 10 can be submerged at desired depths in a large body of water to monitor the $^{12}CO_2$ and $^{13}CO_2$ concentrations as a function of the seasons. It is also contemplated that a plurality of Raman heads 10 can be positioned at a multitude of depths to record desired gases in select locations across the oceans of the globe over an extended time frame (for example and without limitation, years) to derive a broad data base for the entire globe.

It is further contemplated that the disclosed Raman head 10 is well suited for research into the phytosythesis of phytoplankton. These phages are responsible for the production of 50% of $O_2$ by all autotrophic processes in the world, converting $CO_2$ onto organic compounds and molecular oxygen. Furthermore, the metabolism of somewhat larger species such as zooplankton, microorganisms and meroplankton can be studied in natural, polluted and waste water. In another aspect, the health of fish in fisheries depends critically on the oxygen content of the water, which is controlled by the water recycling system. It is contemplated that the Raman head can be beneficial in easily and inexpensively monitoring this environmentally critical oxygen level.

It is also contemplated that $CO_2$ detection with the Raman head 10 at fault lines occurring, for example, at the bottom of oceans, could be a sensitive predictor because the fault lines can release gases, such as $CO_2$, at an early onset of an earth quake. The detection of excess $CO_2$ with the Raman head could provide possible activation of evacuation and/or other safety procedures. It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A Raman head comprising:
   a first, sealed chamber filled with a liquid medium;
   a second chamber open to the surrounding environment, wherein the first and second chambers are separated by a window;
   a multi-pass Raman cell comprising a pair of plano-concave lenses, wherein the planar side of each plano-concave lens is positioned within the first chamber, and the concave side of each plano-concave lens is positioned within the second chamber, and wherein the plano-concave lenses act as spherical mirrors; and
   at least one bellows configured to equalize the pressure in the first sealed chamber and the surrounding environment.

2. The Raman head of claim 1, further comprising an achromatic lens in the first chamber and an adjusting unit configured to position the lens in a desired location.

3. The Raman head of claim 1, further comprising a mirror positioned in the first chamber and configured to reflect a laser beam from the first chamber through the window into the Raman cell.

4. The Raman head of claim 1, wherein the at least one bellows comprises a plurality of bellows.

5. The Raman head of claim 1, wherein the at least one bellows comprises at least one stainless steel bellows.

6. The Raman head of claim 1, wherein the window is a sapphire window.

7. The Raman head of claim 1, wherein the liquid medium comprises distilled water.

* * * * *